US010076652B2

(12) United States Patent
Liu et al.

(10) Patent No.: US 10,076,652 B2
(45) Date of Patent: Sep. 18, 2018

(54) METHOD FOR ULTRASOUND-MEDIATED DELIVERY SYSTEM TO MONITOR MOLECULAR PENETRATION

(71) Applicant: CHANG GUNG UNIVERSITY, Taoyuan (TW)

(72) Inventors: Hao-Li Liu, Taoyuan (TW); Kuo-Chen Wei, Taipei (TW); Pin-Yuan Chen, Taoyuan (TW); Po-Hung Hsu, Tainan (TW); Po-Chun Chu, Taipei (TW); Wen-Yen Chai, Taoyuan (TW); Chung-Yin Lin, Kaohsiung (TW)

(73) Assignee: CHANG GUNG UNIVERSITY, Taoyuan (TW)

( * ) Notice: Subject to any disclaimer, the term of this patent is extended or adjusted under 35 U.S.C. 154(b) by 442 days.

(21) Appl. No.: 14/822,896

(22) Filed: Aug. 10, 2015

(65) Prior Publication Data
US 2017/0043149 A1   Feb. 16, 2017

(51) Int. Cl.
*A61M 37/00* (2006.01)
*A61B 5/00* (2006.01)
(Continued)

(52) U.S. Cl.
CPC ....... *A61M 37/0092* (2013.01); *A61B 5/0035* (2013.01); *A61B 5/055* (2013.01); *A61B 5/4064* (2013.01); *A61B 6/03* (2013.01); *A61B 6/481* (2013.01); *A61B 6/5211* (2013.01); *A61B 5/0042* (2013.01); *A61B 5/14507* (2013.01); *A61B 5/14546* (2013.01); *A61M 2205/3303* (2013.01)

(58) Field of Classification Search
None
See application file for complete search history.

(56) References Cited

U.S. PATENT DOCUMENTS

2010/0143241 A1\*  6/2010  Johnson ............ A61K 41/0028
                                                    424/1.11
2011/0295105 A1\* 12/2011  Konofagou ....... A61M 37/0092
                                                    600/411

(Continued)

OTHER PUBLICATIONS

Burgess et al., "Focused ultrasound-mediated drug delivery through the blood-brain barrier". Expert Rev Neurother. May 2015; 15(5): 477-49.\*

(Continued)

*Primary Examiner* — Katherine Fernandez
*Assistant Examiner* — Yi-Shan Yang
(74) *Attorney, Agent, or Firm* — Cheng-Ju Chiang

(57) ABSTRACT

Methods to use medical imaging to monitor the molecule penetration into CNS during ultrasound-mediated delivery are disclosed. The method states a two-step process to predict the amount of molecular penetration which is based on the observation of medical imaging. The first is to propose a unified exposure input to unify the exposure condition so as to build a transferred relation to imaging index. The second is to propose a unified imaging index to unify the imaging readout so as to build a reliable transferred relation to molecular concentration. Linking these two, the molecular penetration induced by ultrasound irradiation can be estimated from medical imaging with ultrasound exposure conditions and molecular sizes.

20 Claims, 16 Drawing Sheets

(51) Int. Cl.
*A61B 6/03* (2006.01)
*A61B 6/00* (2006.01)
*A61B 5/055* (2006.01)
*A61B 5/145* (2006.01)

(56) References Cited

U.S. PATENT DOCUMENTS

| | | | |
|---|---|---|---|
| 2012/0010502 A1* | 1/2012 | Yang | A61B 5/4839 600/431 |
| 2012/0095325 A1* | 4/2012 | Wei | A61B 5/0042 600/411 |
| 2015/0073260 A1* | 3/2015 | Yang | G01R 33/56308 600/411 |

OTHER PUBLICATIONS

Frullano et al., "A myelin-specific contrast agent for magnetic resonance imaging of myelination". J, Am, Chem. Soc. 2011; 133(6): 1611-1613.*

Patlak et al., "Graphical Evaluation of Blood-to-Brain Transfer Constants from Multiple-Time Uptake Data. Generalizations", Journal of Cerebral Blood Flow and Metabolism, 1985, 5:584-590.*

Chassidim et al., "Quantitative imaging assessment of blood-brain barrier permeability in humans"., Fluids and Barriers of the CNS 2013, 10:9.*

Hynynen et al., "Noninvasive MR imaging-guided focal opening of the blood-brain barrier in rabbits". Radiology. 2001; 220:640-46.*

Chopra et al., "Influence of Exposure Time and Pressure Amplitude on Blood-Brain-Barrier Opening Using Transcranial Ultrasound Exposures". ACS Chem. Neurosci. (2010), 1, 391-398.*

McDannold et al., "Effects of acoustic parameters and ultrasound contrast agent dose on focused-ultrasound induced blood-brain barrier disruption". Ultrasound in Med. & Biol., vol. 34, No. 6, pp. 930-937, 2008.*

Fan et al., "Contrast-Enhanced Ultrasound Imaging for the Detection of Focused Ultrasound-Induced Blood-Brain Barrier Opening". Theranostics 2014, vol. 4, Issue 10, pp. 1014-1025. Published Aug. 1, 2014.*

* cited by examiner

METHOD FOR ULTRASOUND-MEDIATED DELIVERY SYSTEM TO MONITOR MOLECULAR PENETRATION

FIELD OF THE INVENTION

The present invention relates to ultrasound-mediated delivery methods, especially relates to using a series of mathematical models to monitor molecular penetration of drugs into the blood-brain barrier.

BACKGROUND OF THE INVENTION

The blood-brain barrier (BBB) is a specialized structure of capillary in the central nervous system (CNS). The BBB consists of three structures: the cerebral capillary endothelium, the choroid plexus epithelium, and the arachnoid membranes. These structures prevent invasion of external substances or molecules that may affect brain functions from penetrating into brain tissue, but also restrict helpful materials access to brain tissue. CNS diseases are hard to be treated due to that the BBB protects brain parenchyma and completely restricts enhanced-permeability/retention (EPR) effect of therapeutic nanoparticles. The BBB serves as an impenetrable barrier to prohibit the delivery of many effective diagnostic agents or therapeutic medicines, thereby reducing the effects of the treatments for CNS diseases.

In addition, the BBB shows low endocytic activity and absence of fenestrations, thus limits the transcellular transport of molecules. In the physiological role, the BBB excluding hydrophobic and larger molecules (>400 Da) from the CNS should be temporarily turned down, and the BBB should open a local delivery to allow the macromolecular substances diffusing to the brain.

Currently, a number of clinical and preclinical researchers attempt to use chemotherapeutic agents in different ways against brain cancers, the ways including: intravenous injection, interstitial injection/implantation, convection-enhanced delivery (CED), and osmotic blood-brain barrier disruption. As to the interstitial injection/implantation and the CED, they are invasive procedures which rely on surgical operations to perform craniotomy. One major disadvantage of the osmotic blood-brain barrier disruption is that if the BBB was globally disrupted, it may hamper specific drug delivery to brain tumor. The limited use of the intravenous injection is due to the systemic toxicity of the intravenous administered therapeutic agents. It limits the allowable dose to be applied. If the amount of drug exceeds the tolerance dose, it will cause systemic adverse effects to patients. Fortunately, this BBB opening effect has been found that it is temporary and could be reversed, and it has no dangerous effects to the neural cells.

In the other hand, in order to enhance efficiency of the brain drug transportation, one way is using modified lipophilic chemicals or hypertonic solution to infuse through the carotid into the brain. The other way is using focused ultrasound. Comparing to the modified chemicals, the advantage of the focused ultrasound that it is a noninvasive procedure, and it can locally open the BBB and minimize the off-target effect. The BBB opening effect will be reserved within several hours, which is a suitable period for drug release. The focused ultrasound also makes rectified (in intact BBB) or increased EPR (in tumor) effect in the brain, that is possibly to achieve local, temporary and noninvasive chemotherapeutic agent delivery. The focused ultrasound therefore is more competitive and attractive to perform and increase local concentration of therapeutic agents in CNS.

Some researchers use proper ultrasound exposure parameters to successfully induce the intact BBB opening effect, the ultrasound driving at burst-tone in week pressure mode can induce the BBB to open. In additionally, the higher acoustic pressure level had been reported to induce a larger scale of BBB opening, the focused ultrasound exposure at different center frequencies will produce different thresholds to induce BBB opening, and the exposure time and consecutive focused ultrasound exposures have been reported to induce molecular penetration in linearly increasing fashion.

Nowadays, medical practitioners expect that the molecule delivery can be predicted, and a more tailor-made CNS drug delivery plan can be made to make the molecule delivered procedure to be more individualized and personalized (i.e., personalized medicine), but it's still unknown that how to predict the scale of molecular penetration under various molecular sizes with the given focused ultrasound exposure parameters. The ultrasound exposure parameters seem multiple and have no direct link with the delivered molecular concentration. The situation makes the treatment of brain diseases to be difficult, and the results are not predictable and controllable.

SUMMARY OF THE INVENTION

According to the above mentioned viewpoints, the present invention is related to using medical imaging to measure the substance into CNS after performing focused ultrasound (FUS) induced BBB opening.

In this present invention also provides a method for monitoring molecular penetration by an ultrasound-mediated brain drug delivery system, and the method comprises following steps: providing a medical imaging system and an ultrasound system; administering a microbubble agent to the capillary in a brain and concurrently applying the ultrasonic wave to transiently permeate a BBB; determining a unified exposure index (UEI) with multiple exposure parameters of the ultrasound system; applying ultrasound energy by the ultrasound system to open the BBB in a brain; administering a contrast agent to the brain; analyzing multiple imaging data obtained from the medical imaging system to calculate at least one imaging index; determining a unified imaging index (UII) by the at least one imaging index; and incorporating the UEI and the UII to determine a delivered molecular concentration of the contrast agent cross the BBB. Following these steps could estimate the concentration of the delivered molecules into the targeted CNS tissues.

Implementations of this invention may further include one or more of the following features. The medical imaging system comprises a computed tomography equipment and a magnetic resonance imaging equipment. The ultrasound system is a focused ultrasound apparatus.

Implementations of this invention may further include one or more of the following features. The multiple exposure parameters comprise an exposure time, a center frequency, and a pressure.

Implementations of this invention may further include one or more of the following features. The contrast agent could comprise a drug or not, and the drug is to treat neurological diseases and disorders. The drugs' molecular weight range is from 0.1 kDa to 200 kDa.

Implementations of this invention may further include one or more of the following features. The at least one imaging index comprises a first imaging index, a second imaging index, a third imaging index, and a fourth imaging index. The first imaging index represents a molecule penetrating percentage of the contrast agent into the BBB. The second imaging index represents a total signal intensity change in a fixed time period. The third imaging index represents an influx permeability of the contrast agent. The fourth imaging index represents a volume fraction change of the total molecular penetration into the brain. The UEI represents an opening scale of the blood-brain barrier which is induced by the ultrasound system. The UII represents an opening scale of the BBB which are detected by the medical imaging system.

In one embodiment of this invention further provides a specific method for monitoring molecular penetration, and the main idea of the method includes the following steps: providing a dynamic contrast-enhanced magnetic resonance imaging (DCE-MRI) equipment and a focused ultrasound apparatus; administering a microbubble agent to the capillary in a brain and concurrently applying the ultrasonic wave to transiently permeate a BBB; determining a unified exposure index (UEI) with multiple exposure parameters of the focused ultrasound apparatus; applying an ultrasound energy by the focused ultrasound to open the BBB in a brain; administering a contrast agent to the brain; analyzing multiple imaging data obtained from the DCE-MRI equipment and based on pharmacokinetic and pharmacodynamic behavior to calculate at least one imaging index; determining a unified imaging index (UII) by at least one imaging index; and incorporating the UEI and the UII to determine a delivered molecular concentration of the contrast agent cross the BBB.

The at least one imaging index, the UEI, and the UII also could be contributed from a series of mathematical models so as to find the specific concentration of the delivered molecules which transport into the targeted CNS tissues.

Implementations of this invention may further include one or more of the following features. The contrast agent could comprise a drug or not, and the drug is to treat neurological diseases and disorders. The at least one imaging index comprises a first imaging index (II1), a second imaging index (II2), a third imaging index (II3), and a fourth imaging index (II4).

The II1 is described as:

$$\left(\frac{SI_{post} - SI_{pre}}{SI_{pre}} * 100\%\right).$$

The II2 is described as:

$$\left(\frac{\int_t Cpt \cdot dt}{V}\right).$$

The II3 is described as the term of $K_{trans}$ in the calculation of the following function:

$$C_t(t) = v_p C_p(t) + K_{trans} \int_0^\tau C_p(t') \times e^{\left[\frac{-K_{trans}(t-t')}{v_e}\right]} dt'.$$

The II4 is described as term of $v_e$ in the calculation of the following function:

$$C_t(t) = v_p C_p(t) + K_{trans} \int_0^\tau C_p(t') \times e^{\left[\frac{-K_{trans}(t-t')}{v_e}\right]} dt'.$$

The UII is described as: g (II1, II2, II3, II4), the g(.) is a function.

The UEI is described as: f (P, freq, $t_{on}$)=$P^a \times freq^b \times t_{on}$.

The UII and the UEI are integrated to obtain the molecular concentration (Cm), and the Cm is described as: Cm=G (UEI, UII, M W), the G(.) is a function.

The details of aforementioned symbols will be explained clearly in detailed description sections.

The methods of this invention contribute to link the ultrasound exposure parameters and the delivered molecular concentration, and they also contribute to obtain a specific numerical value to make the brain diseases treatment become easier and the results could be controlled. These methods can be further to form software format which could be installed in computers, and provide medical practitioners to use them in a more convenient way.

DETAILED DESCRIPTION OF THE INVENTION

Figure 1:
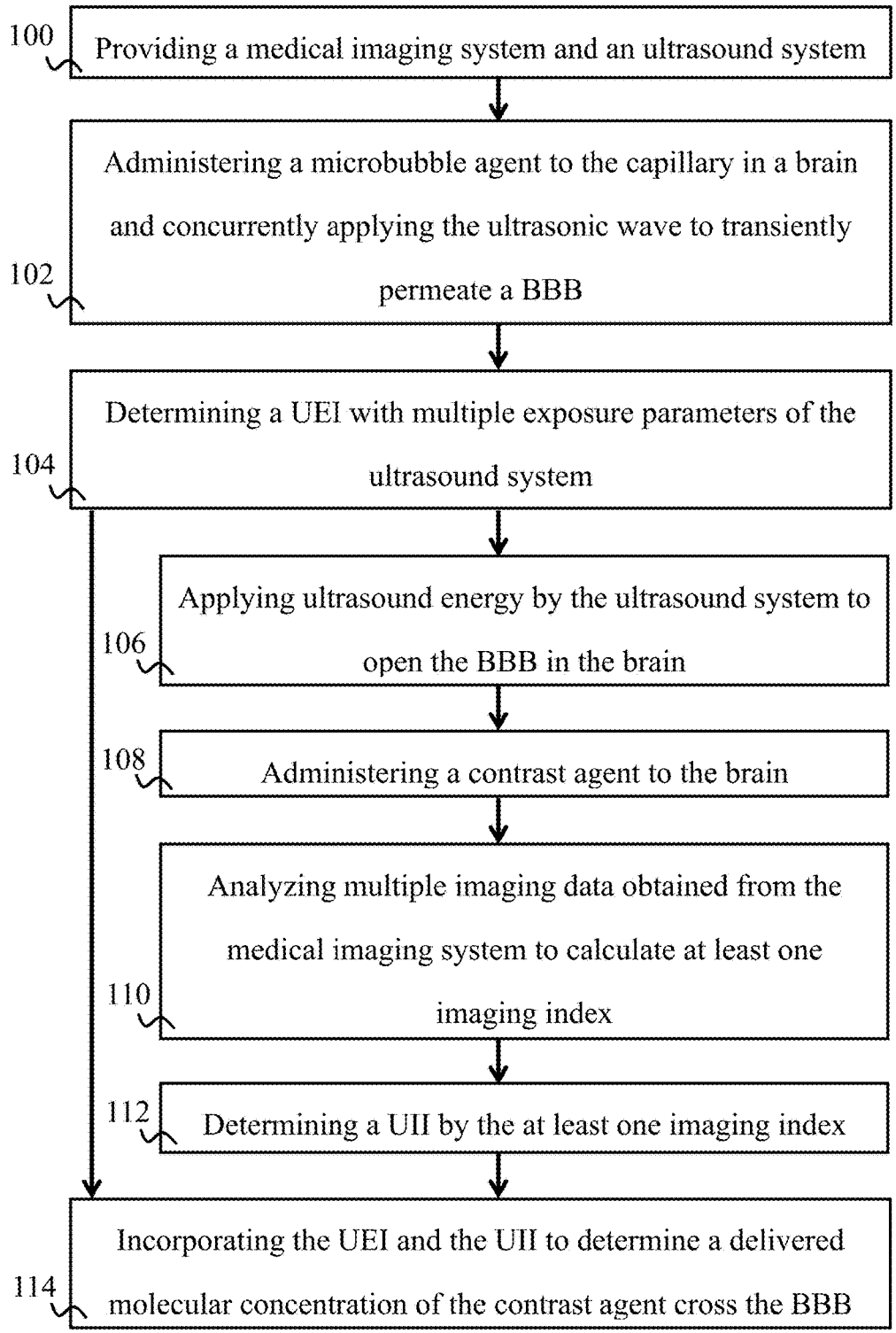
FIG. 1 is a flow chart showing one preferred embodiment of the invention.

Referring to FIG. 1, a method for monitoring molecular penetration by an ultrasound-mediated delivery system. At step 100, providing magnetic resonance imaging (MRI) equipment as an imaging monitoring apparatus and focused ultrasound (FUS) apparatus as an ultrasound energy-transmitting system. At step 102, administering a microbubble agent to a brain capillary that provide a physical effect on the brain capillary to transiently open the blood-brain barrier.

At step 104, determining a unified exposure index (UEI) with multiple exposure parameters of the ultrasound system, said exposure parameters include exposure conditions: including time, center frequency, and pressure.

At step 106 and 108, applying ultrasound energy by the ultrasound system to open a blood-brain barrier, and administering a contrast agent to a brain such as a tumor tissue. The contrast agent could comprise a drug or not, and said drug is to treat neurological diseases and disorders such as Meningitis, Brain abscess, Multiple Sclerosis, Alzheimer's disease, Parkinson's disease, Glioblastoma multiforme. The drug's molecular weight range is from 0.1 kDa to 200 kDa.

At step 110, analyzing multiple imaging data obtained from the medical imaging system to calculate at least one imaging index. The at least one imaging index comprises a first imaging index (II1), a second imaging index (II2), a third imaging index (II3), and a fourth imaging index (II4). The II1 represents a molecule penetrating percentage of the exogenous agent into the BBB immediately. The II2 represents a total signal intensity change in a pre-determined time period. The II3 represents an influx permeability of the contrast agent. The II4 represents an impulse response function.

At step 112 and 114, determining a unified imaging index (UII) by the at least one imaging index, and incorporating the UEI and the UII to determine a delivered molecular concentration of the contrast agent cross the BBB. The UEI represents an opening scale of the blood-brain barrier which is induced by the ultrasound system. The UII represents an opening scale of the BBB which is detected by the medical imaging system.

The idea of above method is to link the UEI and the UII so as to build a reliable transferred relation between molecular concentration and the ultrasound exposure parameters. Furthermore, how to predict a specific molecular penetration by using different molecular weights of the drugs under different ultrasound conditions, and achieving a better personal therapy is presented in the following embodiments.

Figure 2:
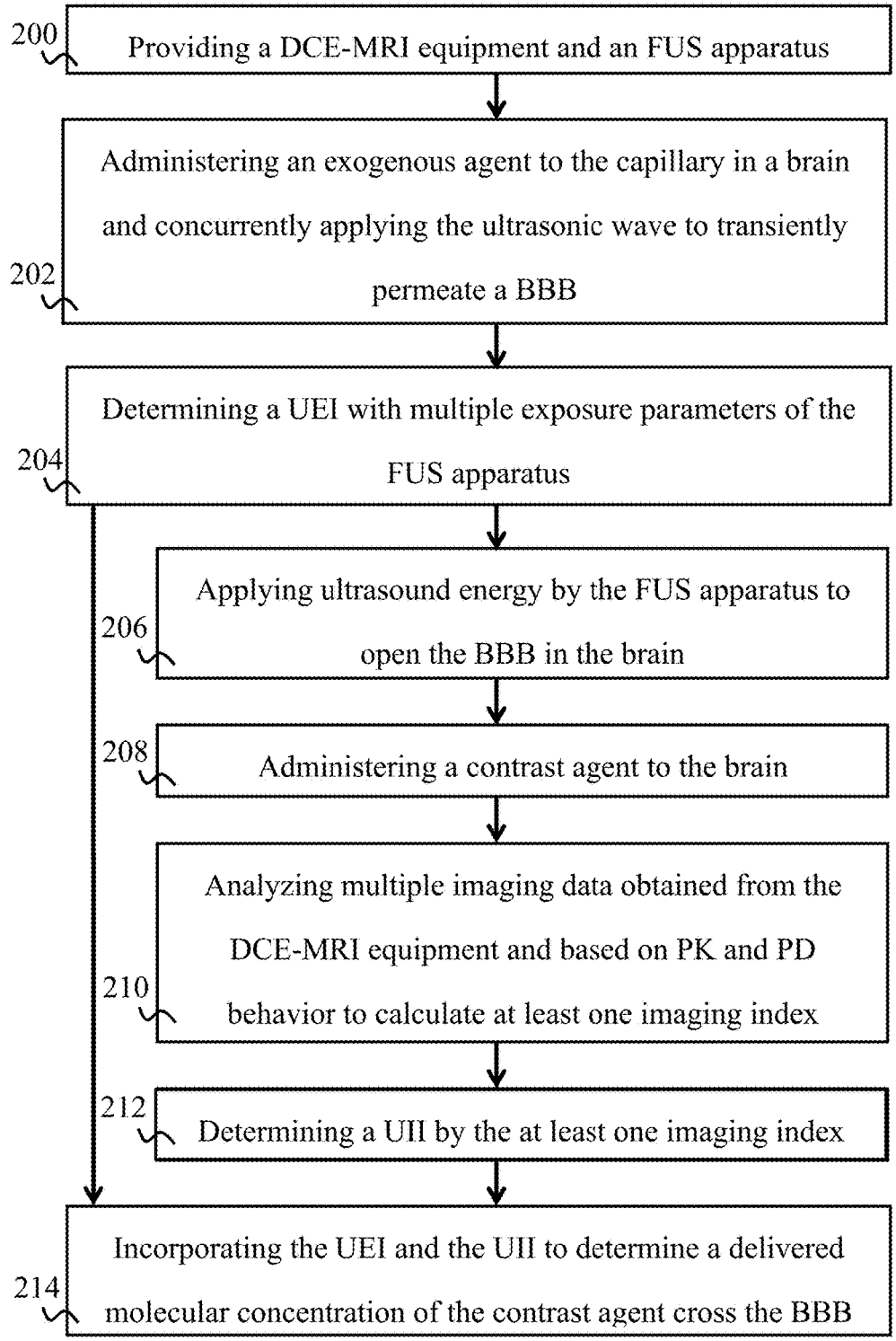
FIG. 2 is a flow chart showing another preferred embodiment of the invention.

Referring to FIG. 2, this invention further provides a specific method for monitoring molecular penetration, it includes the following steps: 200 providing a dynamic contrast-enhanced magnetic resonance (DCE-MRI) imaging equipment and a FUS apparatus; 202 administering a microbubble agent to the capillary in a brain and concurrently applying the ultrasonic wave to transiently permeate a BBB; 204 determining a unified exposure index (UEI) with multiple exposure parameters of the focused ultrasound apparatus; 206 applying ultrasound energy by the focused ultrasound to open the BBB; 208 administering contrast agent to a brain; 210 analyzing multiple imaging data obtained from the DCE-MRI imaging equipment and based on pharmacokinetic and pharmacodynamic behavior to calculate at least one imaging index that comprises a first imaging index (II1), a second imaging index (II2), a third imaging index (II3), and a fourth imaging index (II4); 212 determining a unified imaging index (UII) by the at least one imaging index; and 214 incorporating the UEI and the UII to determine a delivered molecular concentration of the contrast agent cross the BBB.

Figure 3:
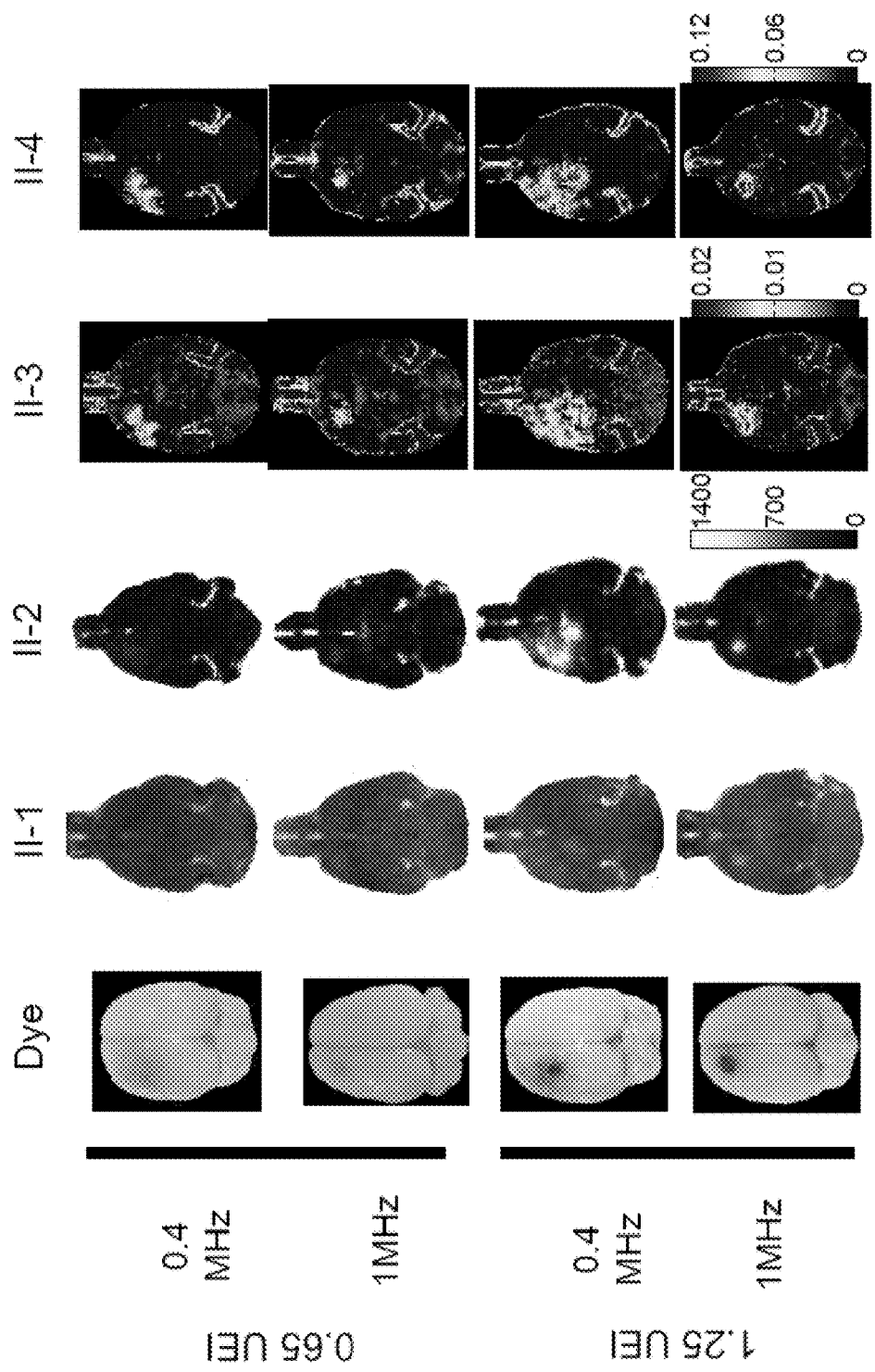
FIG. 3 is dye penetration results of the FUS induced the BBB opening; the results show the imaging indexes which are obtained from contrast enhanced medical imaging.

FIG. 3-16 illustrate presented method for monitoring molecular penetration based on mathematical models. In FIG. 3, it shows a typical DCE-MRI with the information encoded. The dye penetration is induced because FUS induced targeted BBB opening with different acoustic pressure levels and different ultrasound center frequencies. The BBB opening dimensions and sizes are different due to the focal dimension of the ultrasound center frequency. For 0.4 MHz ultrasound, the wavelength in soft tissue is approximately 3.5 mm. For 1 MHz, the wavelength is approximately 1.5 mm. The BBB opening size in 0.4 MHz is larger than that in 1 MHz.

In previous experiment, a number of imaging indexes based on DCE-MRI are obtained. The first imaging index, II1 is the signal intensity (SI) change. The contrast agent is used to detect immediate signal intensity at the BBB opening location, and it is because the MRI contrast agent does not penetrate into CNS. Therefore a signal level change can be obtained from comparing the images before and after the contrast agent injection. The II1 represents the immediate flush scale of the molecule penetrating into the BBB opening site. Next, the second index, II2 is to calculate the accumulation of the signal intensity. It can be calculated by accumulating a pre-determined time period of the total SI changes. The II2 represents the accumulated behavior of the penetrated molecules. Then, the 3rd index, II3 is to calculate the blood-to-brain influx permeability, and the 4th index, II4 is to calculate the volume fraction change due to the BBB opening. II3 and II4 represent the pharmacokinetic and pharmacodynamic changes after transient the BBB opening at the targeted CNS location.

In one embodiment, the II1 also can be calculated as the signal intensity (SI) change of contrast-enhanced T1-weighted (T1-weighted also referred to as T1WI or "spin-lattice" relaxation time) MR image which obtained from before and after performing the contrast agent such as Gd-DTPA administration once, and the focused ultrasound exposure has been conducted to induce a targeted BBB opening. After the SI analysis, a region-of-interest (ROI) was selected from the imaging. This SI change can be calculated as:

$$I1 = \left(\frac{SI_{post} - SI_{pre}}{SI_{pre}} * 100\%\right).$$

The $SI_{post}$ represents SI after Gd-DTPA administration, and the $SI_{pre}$ represents SI before Gd-DTPA administration.

In one embodiment, the II2 can be calculated as the accumulation of the spin-spin relaxometry (R1). After the R1 analysis, the ROI is selected from the R1 map, and compared with the non-enhanced contralateral brain to determine the increase in Gd-DTPA concentration caused by the BBB opening. The area-under-the-curve (AUC) maps are then transferred from a series of time-dependent R1 maps with a period of analyzed time. The purpose of the AUC maps is to determine pharmacodynamic characteristics of Gd-DTPA. The AUC value can be calculated by the following equation:

$$II2 = \left(\frac{\int_t C_{pt} \cdot dt}{V}\right).$$

The $C_{pt}$ is vertical segments under the Gd-DTPA concentration curve area and the V is total ROI volume.

In one embodiment, the II3 and the II4 can be calculated by a compartment model to describe the pharmacokinetic and pharmacodynamic behavior. The model should take the presence of separate extracellular and intravascular compartments into account, and then the time-dependent concentration of the contrast agent in a tissue can be described as:

$II3 = K_{trans}$, $II4 = v_e$, and $K_{trans}$ and $v_e$ can be calculated from the following:

$$C_t(t) = v_p C_p(t) + K_{trans} \int_0^t C_p(t') \times e^{\left[\frac{-K_{trans}(t-t')}{v_e}\right]} dt'$$

$$= v_p C_p(t) + C_p(t) \otimes H(t).$$

The $C_p(t)$ is the contrast agent concentration in the blood plasma, i.e. the arterial input function, the $C_t(t)$ is the contrast concentration in the tissue, the $K_{trans}$ (II3) is the transfer rate constant from the intravascular system to the EES (per unit volume of tissue of the ROI), and the $v_p$ and the $v_e$(II4) are the capillary plasma volume and distribution volume of contrast agent in the EES, respectively. $K_{trans}$ (II3) can also be represented as $K_{ep}$ which means the transfer rate constant from the EES to the intravascular system. The H(t) is the impulse response (or residue) function, and $\otimes$ represents the convolution operation.

In the other hand, the dependency of the BBB opening scale is influenced by multiple exposure parameters. First, considering a specific affected region only, the BBB opening scale is dependent on the center frequency, the ultrasound pressure induce equivalent BBB opening scale is relevantly higher in the higher center frequency than in the lower center frequency, because the center frequency is depend on the tendency of the acoustic cavitation. The acoustic pressure certainly induces different scales of BBB opening. The Higher pressure level has a tendency to induce the higher scale of the BBB opening. Another relevant exposure parameter is the exposure time. The longer exposure time has been explored to induce the higher scale of the BBB opening. The above exposure parameters are all relevant to the opening scale of BBB, and it is successfully to establish a correlation from these FUS exposure parameters, a "unified exposure index (UEI)" is defined in this invention to unify the exposure parameters. The UEI can be considered as the influence of center frequency, acoustic pressure, and exposure time, thus the UEI can be generally defined as: UEI=f (P, freq, $t_{on}$)=$P^a \times freq^b \times t_{on}$.

The P represents the peak pressure (in MPa) and the freq represents the center frequency (in MHz) of FUS exposure, and $t_{on}$ represents the total exposure time (in second). The coefficients a, and b represent the index number to pressure level and center frequency, respectively. Normally, a>b and b is a negative number. Typically, a $\in$[0, 1] and b $\in$[−1, 0].

For example, the UEI could be defined as a simple form with a=1 and b=−0.5, an exposure paradigm setting to pulse repetition frequency (PRF)=1 Hz, burst length=10 ms, and exposure time=100 s equivalents to $t_{on}$=1 s. Therefore, the 1 MHz FUS exposure with 0.5 MPa would totally induce the UEI=0.5.

The UEI serves as the input in this technique, and it should representative and consistent in reflecting the BBB opening scale without the bias to other individual exposure parameter. Since the center frequency and the acoustic pressure are the two most influential exposure parameters. The exposure time has been found that it has linearly correlation with the scale of BBB opening, and it is regardless of the given center frequency or pressure change.

Figure 4A:
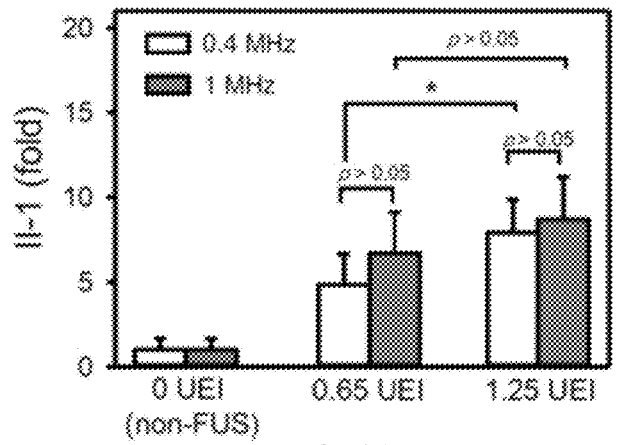
FIG. 4A illustrates the II1 change under different exposure conditions.
Figure 4B:
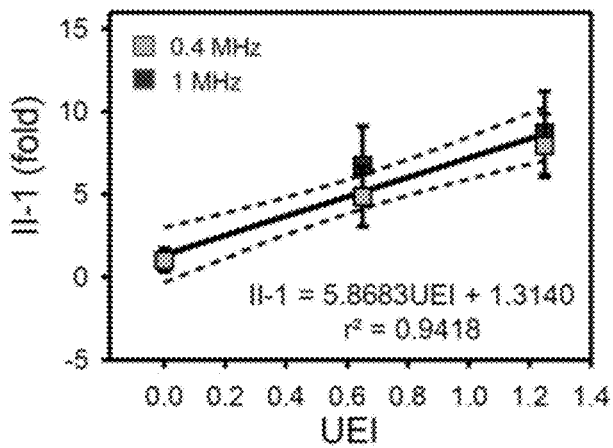
FIG. 4B illustrates the II1 change under given UEI levels (0, 0.65, and 1.3).
Figure 4C:
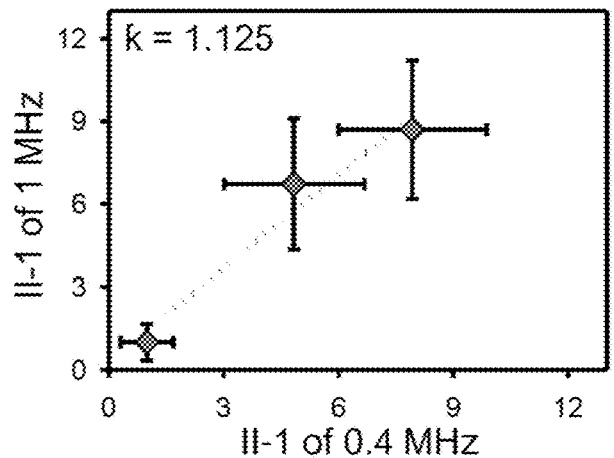
FIG. 4C illustrates the slope K of the results under two different selected UEI arrangements.

In one embodiment shows that using the defined UEI to induce the ultrasound exposure, then evaluating under the defined I1l (see FIG. 4A), and it could be transferred from two various exposure settings (for example, 1st: center frequency=0.4 (MHz), pressure=variable number X (MPa), exposure time=variable number X (sec.); 2nd: center frequency=1 (MHz), pressure=variable number X (MPa), exposure time=variable number X (sec.)). In this example, the given pressure levels are 0.41 and 0.75 MPa in 0.4 MHz; and 0.65 and 1.25 MPa in 1.0 MHz, and then testing four exposure levels. At the same time, these pressure levels also can be transferred from a simple form to obtain the UEIs, a=1, b=−0.5, it only contributes to two different UEI levels of 0.65 and 1.25, respectively (0.41 MPa in 0.4 MHz, and 0.65 MPa in 1.0 MHz contribute to UEI is 0.65; 0.75 MPa in 0.4 MHz, and 1.25 MPa in 1.0 MHz contribute to UEI is 1.2). In FIG. 4B, it is observed on the identical UEIs (dotted line) and defined UEIs (solid line), and the result shows the induced brain permeability change of Ill under defined UEIs is approximately identical (The correlation coefficient $r^2$ is 0.9418). These both confirm the usefulness of using Il1 as an index to monitor the brain permeability change, and the validity of using UEI to unify different input exposure parameters to be one input. In FIG. 4C shows the slope K of the results under different exposure conditions. In this case, the slope K is 1.125 is closer to 1 that means the same UEI caused by different FUS will be closer.

Figure 5A:
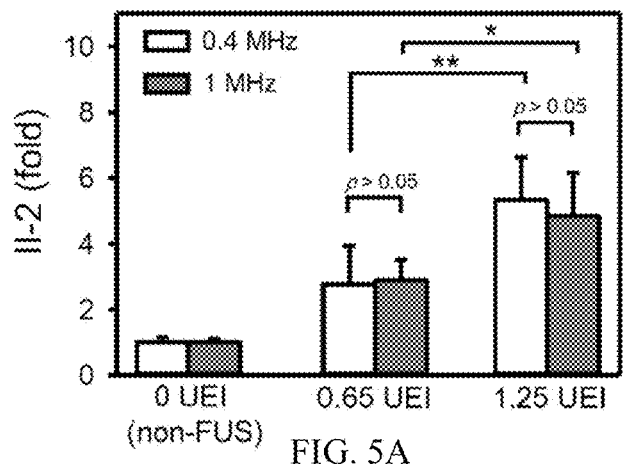
FIG. 5A illustrates the II2 change under different exposure conditions.
Figure 5B:
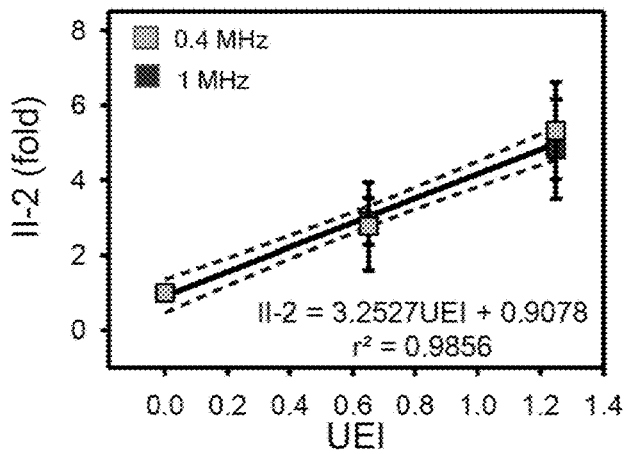
FIG. 5B illustrates the II2 change under given UEI levels (0, 0.65, and 1.3).
Figure 5C:
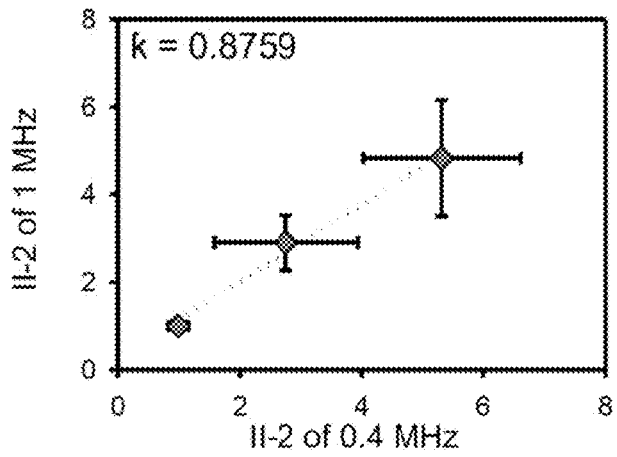
FIG. 5C illustrates the slope K of the results under two different selected UEI arrangements.

In one embodiment shows that using the defined UEI to induce the ultrasound exposure, then evaluating under the defined II2 (see FIG. 5A), and it could be transferred from two various exposure settings (for example, 1st: center frequency=0.4 (MHz), pressure=variable number X (MPa), exposure time=variable number X (sec.); 2nd: center frequency=1 (MHz), pressure=variable number X (MPa), exposure time=variable number X (sec.)). In this example, the given pressure levels are 0.41 and 0.75 MPa in 0.4 MHz; and 0.65 and 1.25 MPa in 1.0 MHz, and then testing four exposure levels. At the same time, these pressure levels also can be transferred from a simple form to obtain the UEIs, a=1, b=−0.5, it only contributes to two different UEI levels of 0.65 and 1.25, respectively (0.41 MPa in 0.4 MHz, and 0.65 MPa in 1.0 MHz contribute to UEI is 0.65; 0.75 MPa in 0.4 MHz, and 1.25 MPa in 1.0 MHz contribute to UEI is 1.2). In FIG. 5B, it is observed on the identical UEIs (dotted line) and defined UEIs (solid line), and the result shows the induced brain permeability change of II2 under defined UEI is approximately identical (The correlation coefficient $r^2$ is 0.9856). These both confirm the usefulness of using II2 as an index to monitor the brain permeability change, and the validity of using UEI to unify different input exposure parameters to be one input. In FIG. 5C shows the slope K of the results under different exposure conditions. In this case, the slope K is 0.8759 is closer to 1 that means the same UEI caused by different FUS will be closer.

Figure 6A:
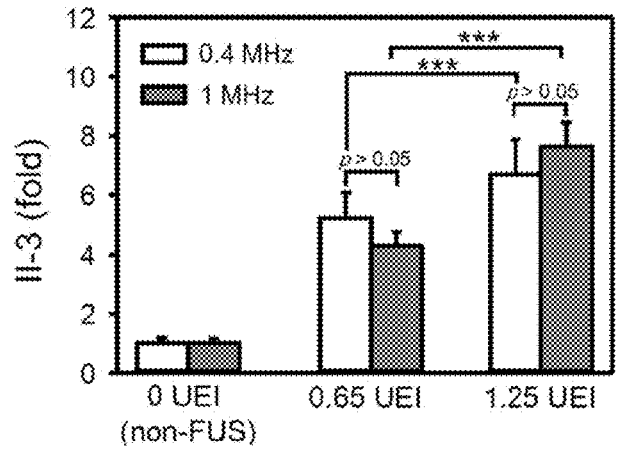
FIG. 6A illustrates the II3 change under different exposure conditions.
Figure 6B:
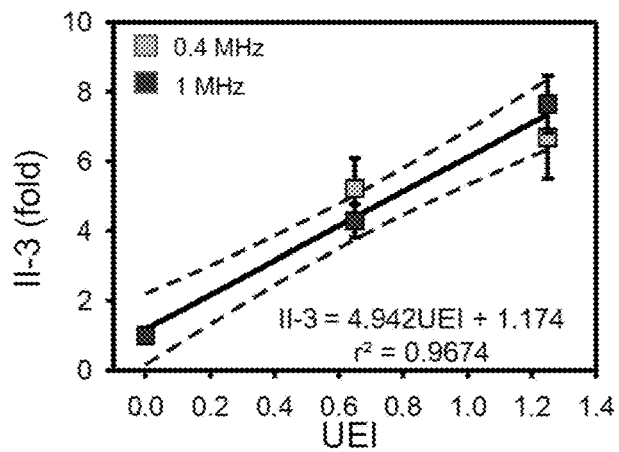
FIG. 6B illustrates the II3 change under given UEI levels (0, 0.65, and 1.3).
Figure 6C:
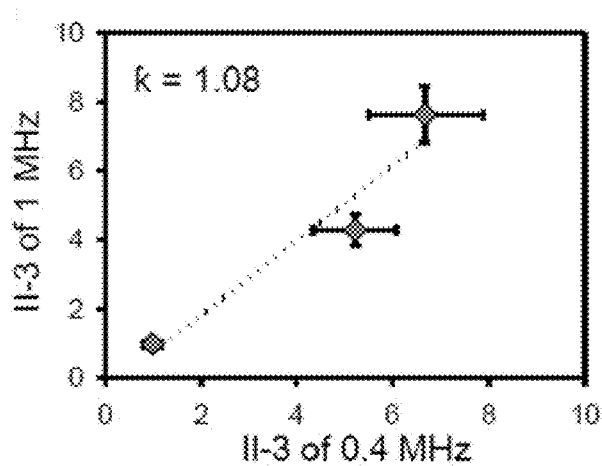
FIG. 6C illustrates the slope K of the results under two different selected UEI arrangements.

In one embodiment shows that using the defined UEI to induce the ultrasound exposure, then evaluating under the defined II3 (see FIG. 6A), and it could be transferred from two various exposure settings (for example, 1st: center frequency=0.4 (MHz), pressure=variable number X (MPa), exposure time=variable number X (sec.); 2nd: center frequency=1 (MHz), pressure=variable number X (MPa), exposure time=variable number X (sec.)). In this example, the given pressure levels are 0.41 and 0.0.75 MPa in 0.4 MHz; and 0.65 and 1.25 MPa in 1.0 MHz, and then testing four exposure levels. At the same time, these pressure levels also can be transferred from a simple form to obtain the UEIs, a=1, b=−0.5, it only contributes to two different UEI levels of 0.65 and 1.25, respectively (0.41 MPa in 0.4 MHz, and 0.65 MPa in 1.0 MHz contribute to UEI is 0.65; 0.75 MPa in 0.4 MHz, and 1.25 MPa in 1.0 MHz contribute to UEI is 1.2). In FIG. 6B, it is observed on the identical UEIs (dotted line) and defined UEIs (solid line), and the result shows the induced brain permeability change of II3 under defined UEI is approximately identical (The correlation coefficient $r^2$ is 0.9674). These both confirm the usefulness of using II3 as an index to monitor the brain permeability change, and the validity of using UEI to unify different input exposure parameters to be one input. In FIG. 6C shows the slope K of the results under different exposure conditions. In this case, the slope K is 1.08 is closer to 1 that means the same UEI caused by different FUS will be closer.

Figure 7A:
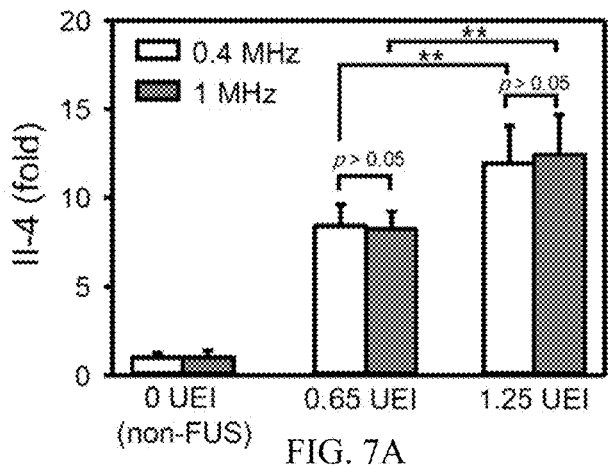
FIG. 7A illustrates the II4 change under different exposure conditions.
Figure 7B:
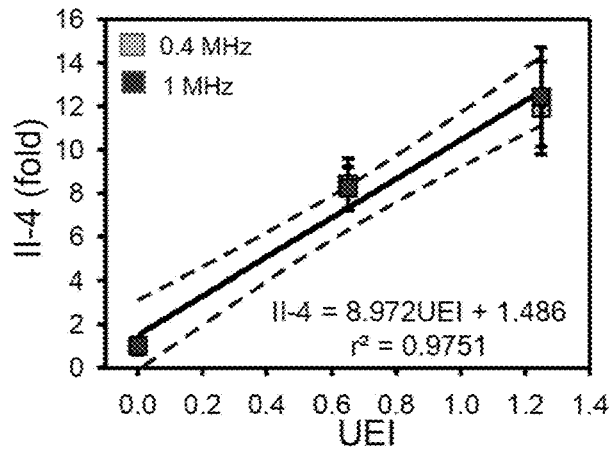
FIG. 7B illustrates the II4 change under given UEI levels (0, 0.65, and 1.3) but transferred from two various exposure settings.
Figure 7C:
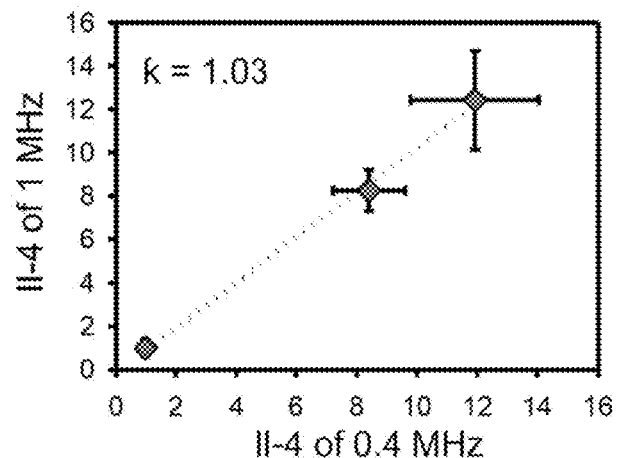
FIG. 7C illustrates the slope K of the results under two different selected UEI arrangements.

In one embodiment shows that using the defined UEI to induce the ultrasound exposure, then evaluating under the defined II4 (see FIG. 7A), and it could be transferred from two various exposure settings (for example, 1st: center frequency=0.4 (MHz), pressure=variable number X (MPa), exposure time=variable number X (sec.); 2nd: center frequency=1 (MHz), pressure=variable number X (MPa), exposure time=variable number X (sec.)). In this example, the given pressure levels are 0.41 and 0.75 MPa in 0.4 MHz; and 0.65 and 1.25 MPa in 1.0 MHz, and then testing four exposure levels. At the same time, these pressure levels also can be transferred from a simple form to obtain the UEIs, a=1, b=−0.5, it only contributes to two different UEI levels of 0.65 and 1.25, respectively (0.41 MPa in 0.4 MHz, and 0.65 MPa in 1.0 MHz contribute to UEI is 0.65; 0.75 MPa in 0.4 MHz, and 1.25 MPa in 1.0 MHz contribute to UEI is 1.2). In FIG. 7B, it is observed on the identical UEIs (dotted line) and defined UEIs (solid line), and the result shows the induced brain permeability change of II4 under defined UEI is approximately identical (The correlation coefficient $r^2$ is 0.9751). These both confirm the usefulness of using II4 as an index to monitor the brain permeability change, and the validity of using UEI to unify different input exposure parameters to be one input. In FIG. 7C shows the slope K of the results under different exposure conditions. In this case, the slope K is 1.03 is closer to 1 that means the same UEI caused by different FUS will be closer.

Figure 8A:
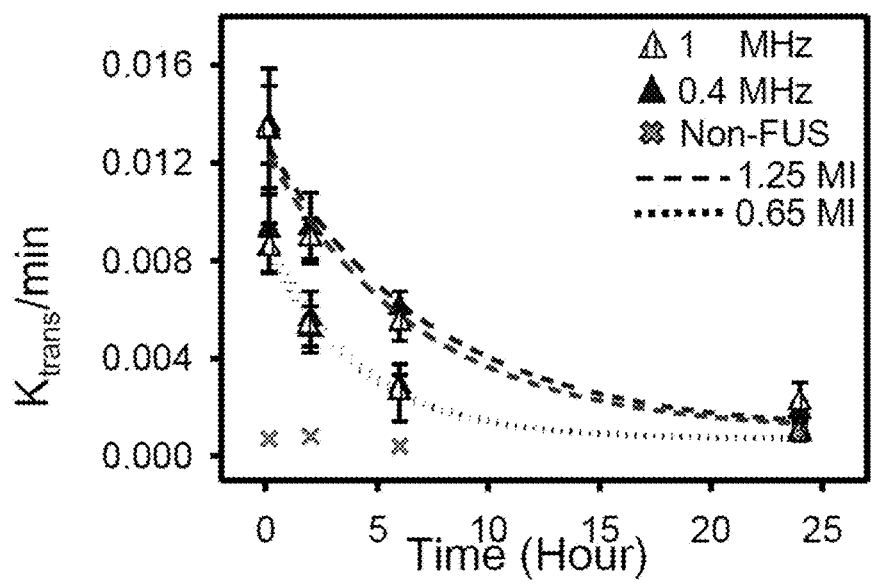
FIG. 8A illustrates the $K_{trans}$ change over time under different exposure conditions.
Figure 8B:
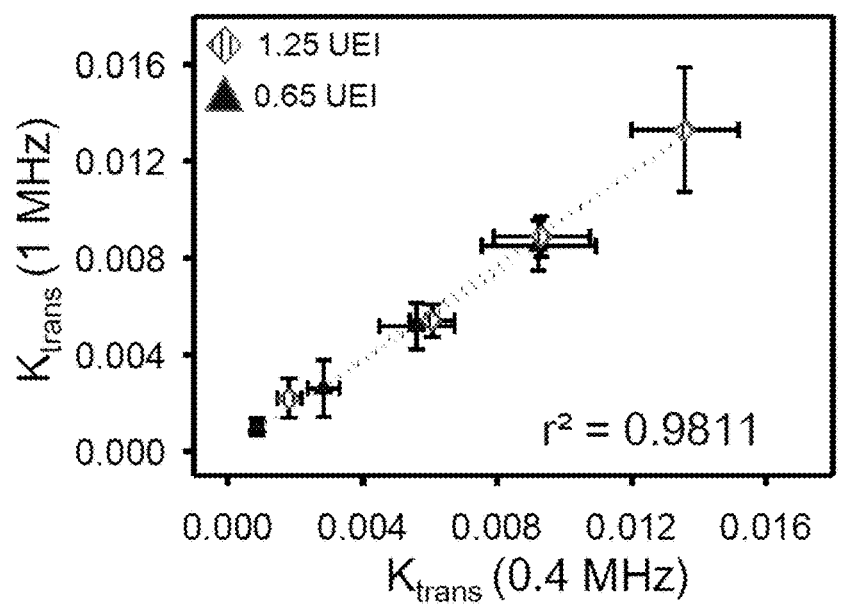
FIG. 8B illustrates the correlation coefficient $r^2$ of the $K_{trans}$ under defined UEIs and different exposure conditions.
Figure 9A:
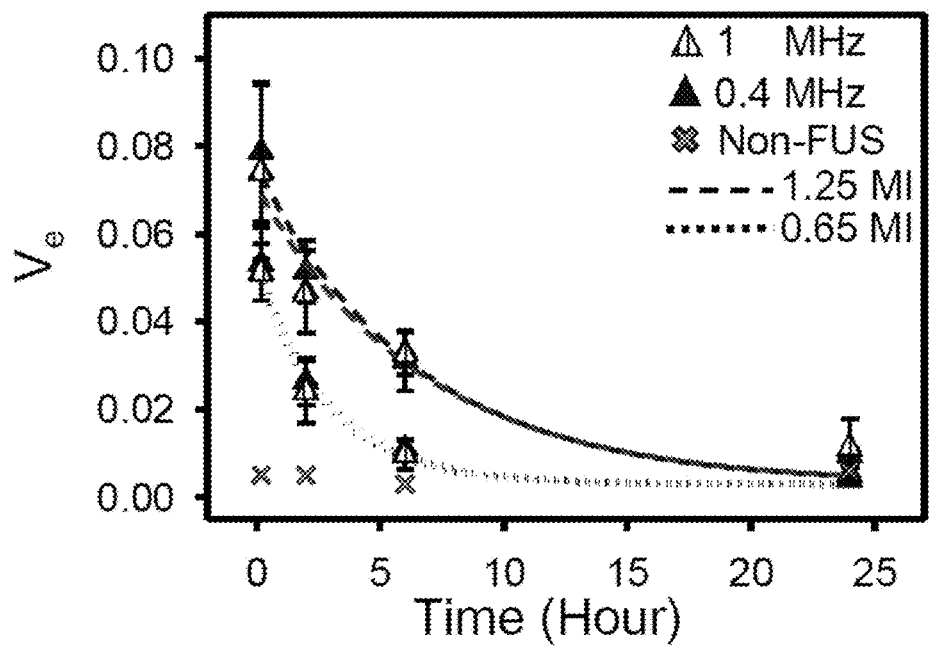
FIG. 9A illustrates the $v_e$ change over time under different exposure conditions.
Figure 9B:
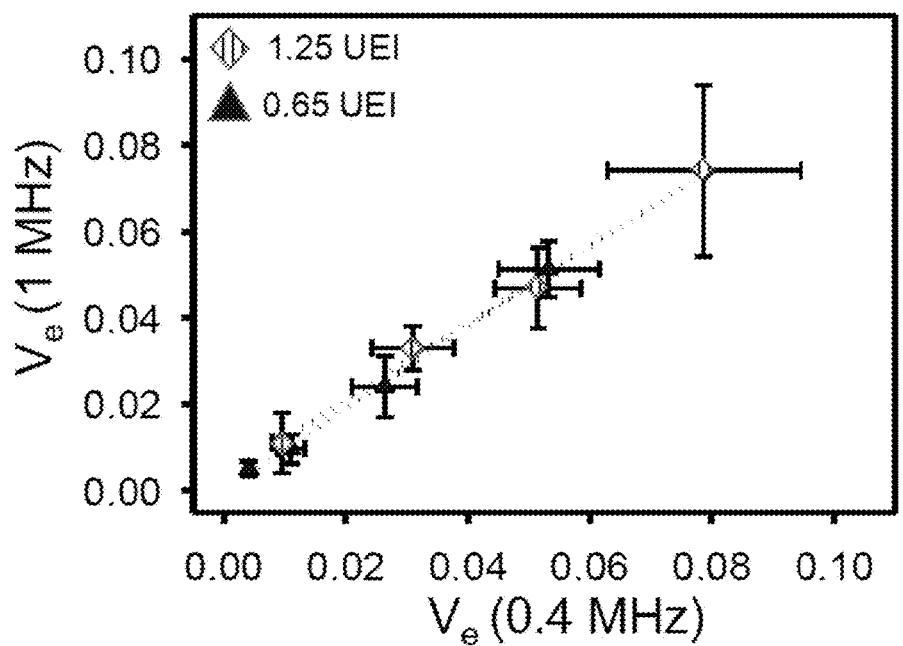
FIG. 9B illustrates the correlation coefficient $r^2$ of the $v_e$ under defined UEIs and different exposure conditions.

The above embodiments show that a properly given UEI can be considered as a representative input to describe the scale of BBB opening under the different imaging indexes. Since the FUS induced BBB opening is a transient process, so the UEI would not hold at a certain point (for example, immediately change after the BBB has been opened), but it seems to hold for the entire dynamic BBB closure process. FIGS. 8A and 9A show two UEIs (0.65 and 1.25) has been applied, and testing separately under two exposure frequencies of 0.4 and 1.0 MHz. In this demonstration, the II3 and II4 are used to evaluate the in-vivo exposure monitoring since these two indexes can be better to describe the transient kinetic and dynamic behavior change. From FIGS. 8B and 9B, it is observed that the higher unified exposure index indeed contribute to the higher $K_{trans}$ and $V_e$ change, but it can be clearly seen that the change is only dependent to the UEI and the gradual BBB disclosure behavior. During this dynamics, it is all independent to the pressure level or center frequency.

The above embodiments show that the described invention is intent to unify the FUS exposure at the first procedure under given four imaging indexes. It shows that a rigid relationship between the UEI and these imaging index. In the second procedure will show a relationship between UEI to UII while considering various sizes of the penetrated molecular substances, and how this relationship can be built.

First, there are three testing substances, and their molecular size spreading from 1 to nearly 150 kDa are employed in second procedure. Three substances are Gd-DTPA, Evans blue, and Bevacizumab.

Gd-DTPA denoted as molecule 1 is 550-743 Da. It is a magnetic resonance contrast agent that is often used to evaluate BBB abnormalities such as stroke or brain tumors. For confirming the invention to provide molecular penetration prediction, the Gd-DTPA serving as a small molecule is quantified to verify the accuracy of this invention.

Evans blue denoted as molecule 2 is a commonly used tissue dye, and its original size is 960 Da, but since it has a very high affinity for serum albumin, it becomes an albumin bound form to expand its size about 70 kDa. It has been used as a viability assay to assess the permeability of the blood-brain barrier to macromolecules for a long time, because the albumin-bound Evans blue cannot cross the barrier, but when the BBB has been opened, the albumin-bound Evans blue can enter the CNS. For confirming the invention to provide molecular penetration prediction, the Evans blue serving as an intermediate molecule is quantified to verify the accuracy of this invention.

Bevacizumab denote as molecule 3 (Its trade name Avastin, Genentech In., Roche) is an angiogenesis inhibitor, and its molecular weight is 149 kDa and it used to slow the growth of new blood vessels. Avastin is a recombinant humanized monoclonal antibody that blocks angiogenesis by inhibiting vascular endothelial growth factor A (VEGF-A). VEGF-A is a chemical signal that stimulates angiogenesis in a variety of diseases, especially in cancer. Avastin is approved to treat glioblastoma (GBM) in many countries when it taken alone in adult patients whose cancer has progressed after prior treatment (recurrent GBM). For confirming the invention to provide molecular penetration prediction, the Avastin serving as large molecule is quantified to verify the accuracy of this invention.

Figure 10A:
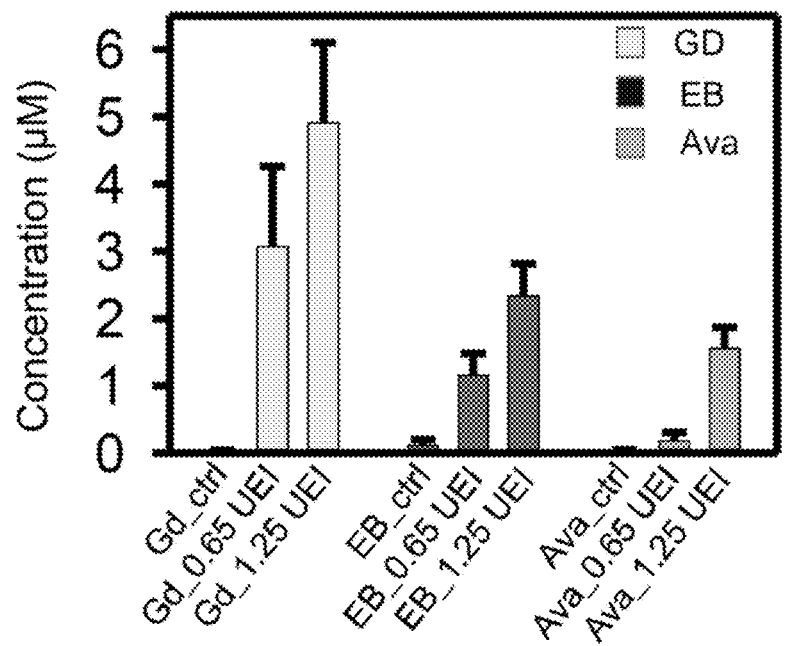
FIG. 10A illustrates the measured molecular penetration under different exposure conditions (UEI is set to 0, 0.65, and 1.25).
Figure 10B:
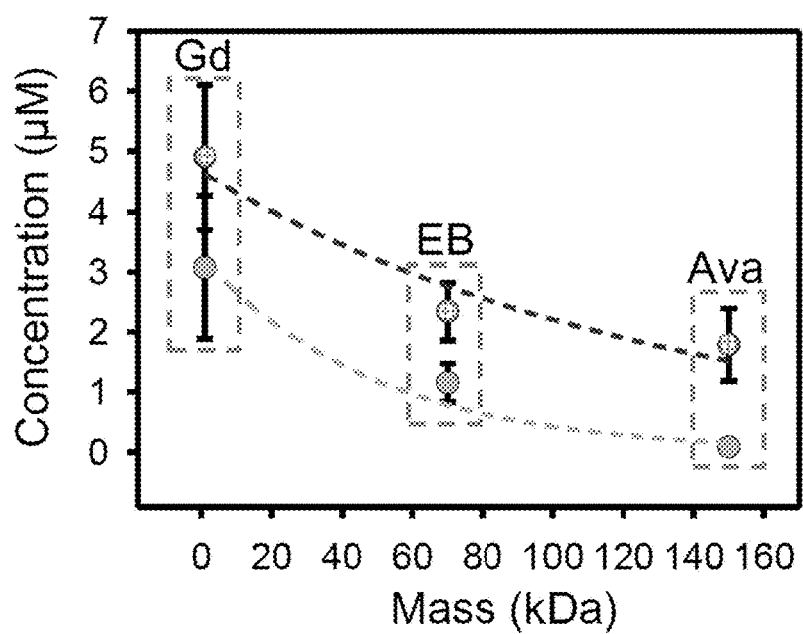
FIG. 10B illustrates the measured molecular penetration under different molecular ranges (UEI is set to 0, 0.65, and 1.25).

FIGS. 10A and 10B are about that selected the UEI ranging of 0.65 and 1.25 for testing, and under testing the center frequency of only 0.4 MHz is employed. FIG. 10A illustrates the measured molecular penetration (molecule 1-3) of different exposure conditions (UEI set to 0, 0.65, and 1.25). FIG. 10B illustrates the measured molecular penetration (molecule 1-3) of different molecular ranges (UEI set to 0, 0.65, and 1.25). These measurement results will be compared with the final predict results.

Figure 11:
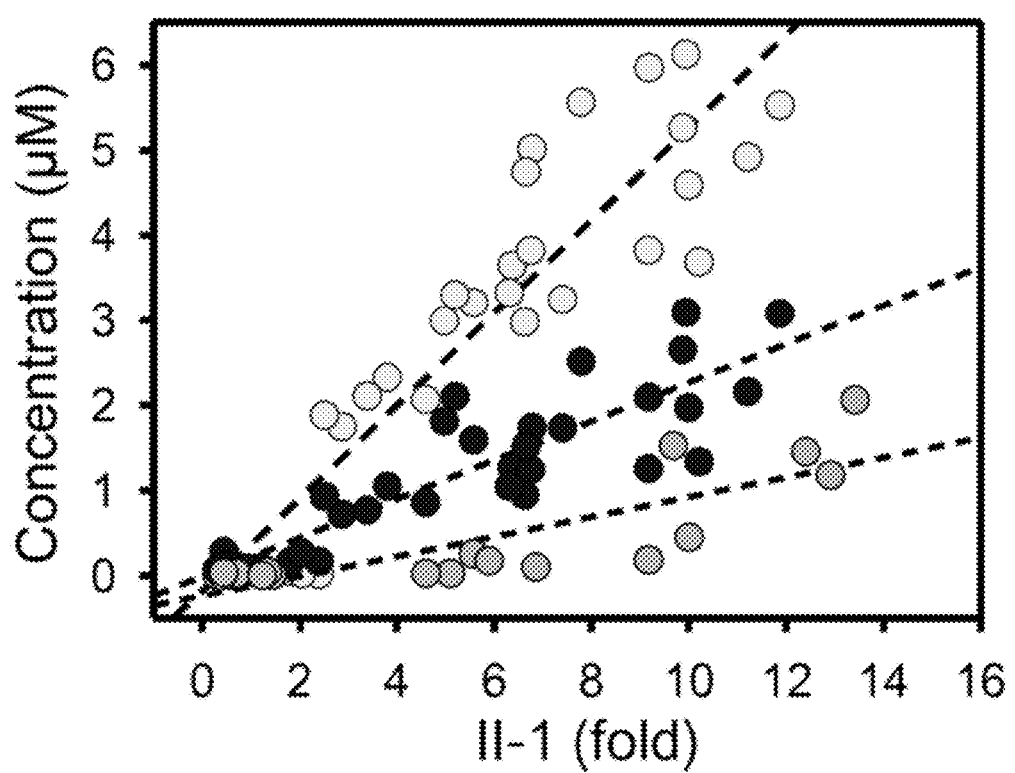
FIG. 11 is the correlation between the molecular penetration of molecule 1-3 (molecular weights are 1, 67, and 150 kDa) and the II1. The range of different UEI is 0-1.25. In this figure, light spots are molecule 1, black spots are molecule 2, and gray spots are molecule 3.

FIG. 11 shows the measured concentrations of molecules 1-3 using the II1 under the given range of UEI. The molecule 1 has the highest penetration because of its small molecular size (1 kDa; the predicted concentration range is 1.7 to 6.2 µM during UEI ranging of 0.65-1.25). The correlation between II1 and the molecule 1 penetration can be derived as: $C_{M1}=0.544 \cdot II_{-1}-0.181$, with the correlation of $r^2=0.874$, the $C_{M1}$ is the concentration of molecule 1. The molecule 2 is observed to have an intermediate molecular penetration (67 kDa; the predicted concentration range is 0.7 µM to 3.1 µM during UEI ranging of 0.65-1.25). The correlation between II1 and the molecule 2 penetration can be derived as: $C_{M2}=0.228 II_{-1}-0.011$, with the correlation of $r^2=0.798$, the $C_{M2}$ is the concentration of molecule 2. The molecule 3 is observed to have the least molecular penetration, because it is the largest molecular size among three (150 kDa; the predicted concentration range is 0.02 µM to 2.1 µM during UEI ranging of 0.65-1.25). The correlation between II1 and the molecule 3 penetration can be derived as: $C_{M3}=0.116 \cdot II_{-1}-0.239$, with the correlation of $r^2=0.678$, the $C_{M3}$ is the concentration of molecule 3. Using II1 as an imaging index to reflect the molecular penetration. Combining with the first procedure, that is able to further calibrate the relationship (using II1) between UEI with molecular penetration at least ranging of 1-150 kDa.

Figure 12:
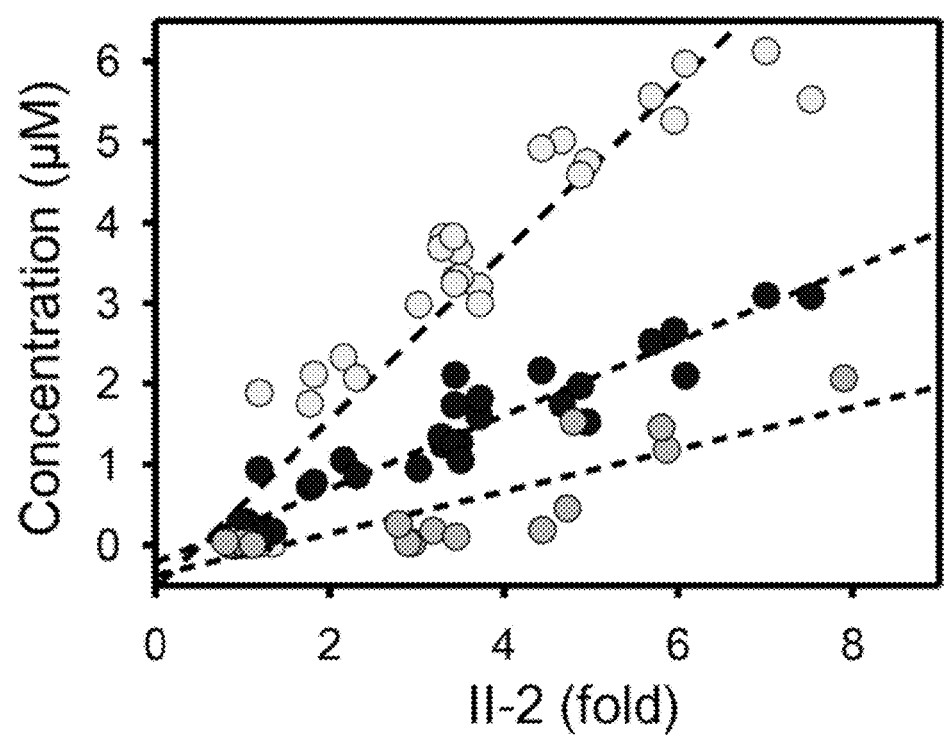
FIG. 12 is the correlation between the molecular penetration of molecule 1-3 (molecular weights are 1, 67, and 150 kDa) and the II2. The range of different UEI is 0-1.25. In this figure, light spots are molecule 1, black spots are molecule 2, and gray spots are molecule 3.

FIG. 12 shows the measured concentrations of molecules 1-3 using the II2 under the given UEI. The molecule 1 again has the highest penetration (the predicted concentration range is 1.7 µM to 6.2 µM during UEI ranging of 0.65-1.25), and the correlation between II2 and molecule 1 penetration can be derived as: $C_{M1}=1.042 \cdot II_{-2}-0.536$, with the correlation of $r^2=0.914$, the $C_{M1}$ is the concentration of molecule 1. The molecule 2 has intermediate molecular penetration (the predicted concentration range is 0.7 µM to 3.1 µM during UEI ranging of 0.65-1.25), and the correlation between II2 and the molecule 2 penetration can be derived as: $C_{M2}=0.457 \cdot II_{-2}-0.221$, with the correlation of $r^2=0.917$, the $C_{M2}$ is the concentration of molecule 2. The molecule 3 has the least molecular penetration (the predicted concentration range is 0.02 µM to 2.1 µM during UEI ranging of 0.65-1.25). The correlation between II2 and the molecule 3 penetration can be derived as: $C_{M3}=0.26 \cdot II_{-2}-0.379$, with the correlation of $r^2=0.738$, the $C_{M3}$ is the concentration of molecule 3. That is able to further calibrate the relationship (using II2) between UEI with molecular penetration at least ranging of 1-150 kDa.

Figure 13:
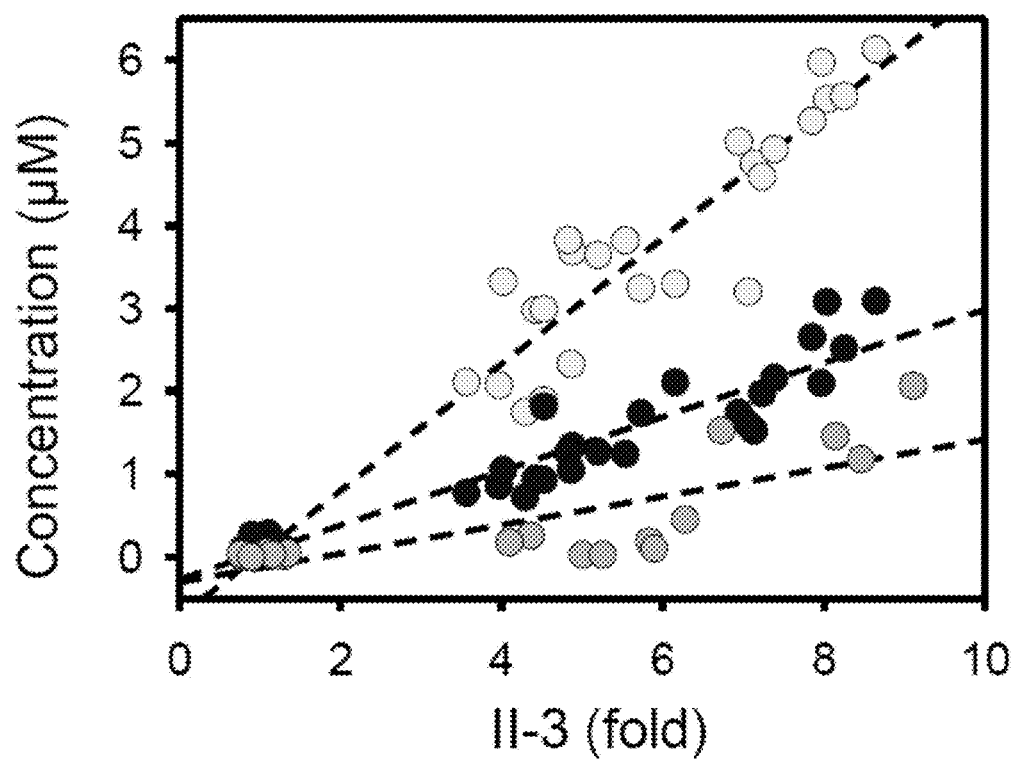
FIG. 13 is the correlation between the molecular penetration of molecule 1-3 (molecular weights are 1, 67, and 150 kDa) and the II3. The range of different UEI is 0-1.25. In this figure, light spots are molecule 1, black spots are molecule 2, and gray spots are molecule 3.

FIG. 13 shows the measured concentrations of molecules 1-3 using the II3 under the given UEI. The molecule 1 again has the highest penetration (the predicted concentration range is 1.7 µM to 6.2 µM during UEI ranging of 0.65-1.25), and the correlation between II3 and molecule 1 penetration can be derived as: $C_{M1}=0.762 \cdot II_{-3}-0.726$, with the correlation of $r^2=0.948$, the $C_{M1}$ is the concentration of molecule 1. The molecule 2 has intermediate molecular penetration (the predicted concentration range is 0.7 µM to 3.1 µM during UEI ranging of 0.65-1.25), and the correlation between II3 and the molecule 2 penetration can be derived as: $C_{M2}=0.326 \cdot II_{-3}-0.271$, with the correlation of $r^2=0.907$, the $C_{M2}$ is the concentration of molecule 2. The molecule 3 has the least molecular penetration (the predicted concentration range is 0.02 µM to 2.1 µM during UEI ranging of 0.65-1.25). The correlation between II3 and the molecule 3 penetration can be derived as: $C_{M3}=0.171 \cdot II_{-3}-0.303$, with the correlation of $r^2=0.606$, wherein the $C_{M3}$ is the concentration of molecule 3. That is able to further calibrate the relationship (using II3) between UEI with molecular penetration at least ranging of 1-150 kDa.

Figure 14:
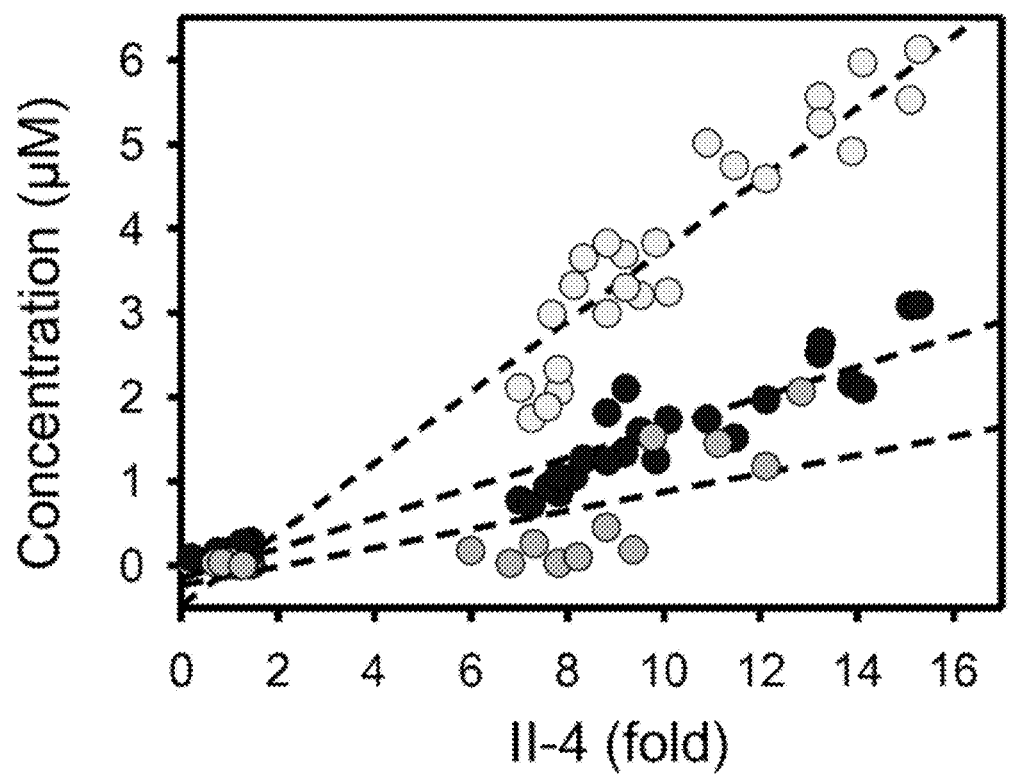
FIG. 14 is the correlation between the molecular penetration of molecule 1-3 (molecular weights are 1, 67, and 150 kDa) and the II4. The range of different UEI is 0-1.25. In this figure, light spots are molecule 1, black spots are molecule 2, and gray spots are molecule 3.

FIG. 14 shows the measured concentrations of molecules 1-3 using the II4 under the given UEI. The molecule 1 again has the highest penetration (the predicted concentration range is 1.7 µM to 6.2 µM during UEI ranging of 0.65-1.25), and the correlation between II4 and molecule 1 penetration can be derived as: $C_{M1}=0.422 \cdot II_{-4}-0.47$, with the correlation of $r^2=0.962$, the $C_{M1}$ is the concentration of molecule 1. The molecule 2 has intermediate molecular penetration (the predicted concentration range is 0.7 µM to 3.1 µM during UEI ranging of 0.65-1.25), and the correlation between II4 and the molecule 2 penetration can be derived as: $C_{M2}=0.179 \cdot II_{-4}-0.155$, with the correlation of $r^2=0.911$, wherein the $C_{M2}$ is the concentration of molecule 2. The molecule 3 has the least molecular penetration (the predicted concentration range is 0.02 µM to 2.1 µM during UEI ranging of 0.65-1.25). The correlation between II4 and the molecule 3 penetration can be derived as: $C_{M3}=0.11 \cdot II_{-4}-0.235$, with the correlation of $r^2=0.56$, the $C_{M3}$ is the concentration of molecule 3. That is able to further calibrate the relationship (using II4) between UEI with molecular penetration at least ranging of 1-150 kDa.

The concept of imaging indexes to serve as monitors is useful, especially intending to use in-vivo imaging to monitor the opening scale of the BBB that is induced by FUS, and these results show that all imaging indexes have their unique feature in BBB opening scale evaluation and molecular penetration prediction. Summarizing the four imaging indexes in molecular penetration, it is assumed to have the most robust concentration prediction. Therefore, introducing the concept in this invention of the "unified imaging index (UII)" to interrogate all the imaging indexes. It will provide a more comprehensive monitoring and evaluation method for making the prediction of the molecular penetration that can be performed better. In present invention, the UII can be defined as a function with the inputs which include the four imaging indexes as:

$$UII=g(II1,II2,II3,II4).$$

The g(•) is a designated function. in one embodiment, the UII can be defined as the linear weighted combination of the four imaging indexes as:

$$UII=w1 \cdot II1^{c1}+w2 \cdot II2^{c2}+w3 \cdot II3^{c3}+w4 \cdot II4^{c4}.$$

The $w_1$ to $w_4$ and the $c_1$ to $c_4$ represent the weight and weighted factor of the power index, II1 to II4, respectively.

Figure 15:
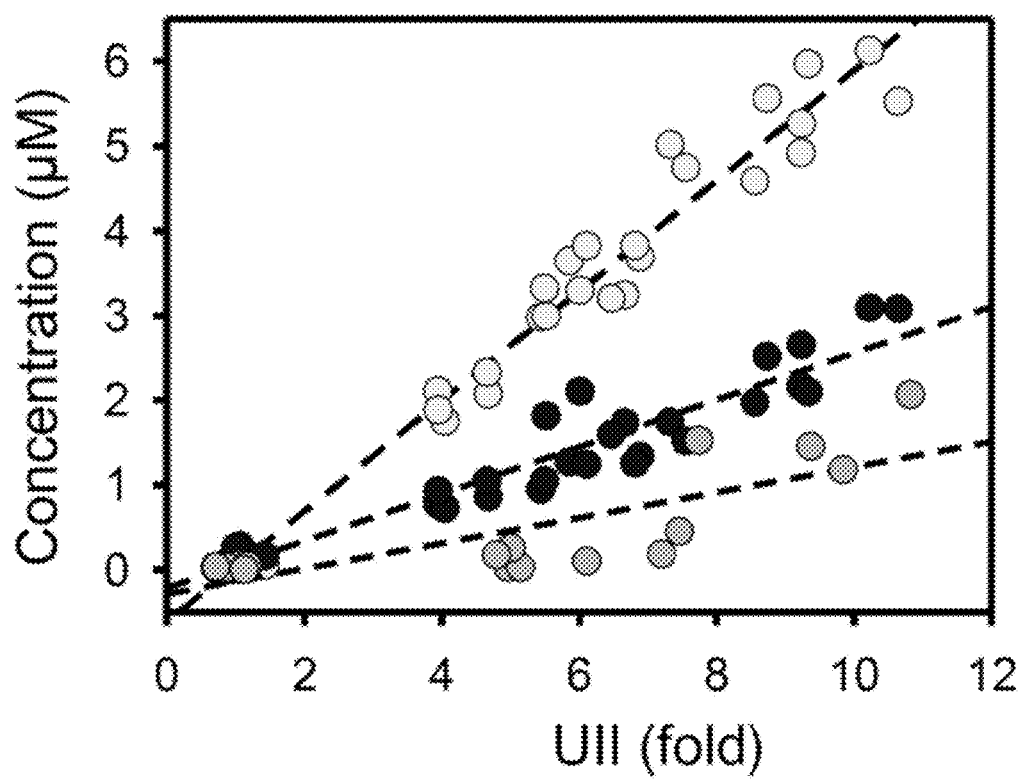
FIG. 15 is the correlation between the molecular penetration of molecule 1-3 (molecular weights are 1, 67, and 150 kDa) and the UII. The range of different UEI is 0-1.25. In this figure, light spots are molecule 1, black spots are molecule 2, and gray spots are molecule 3.
Figure 16:
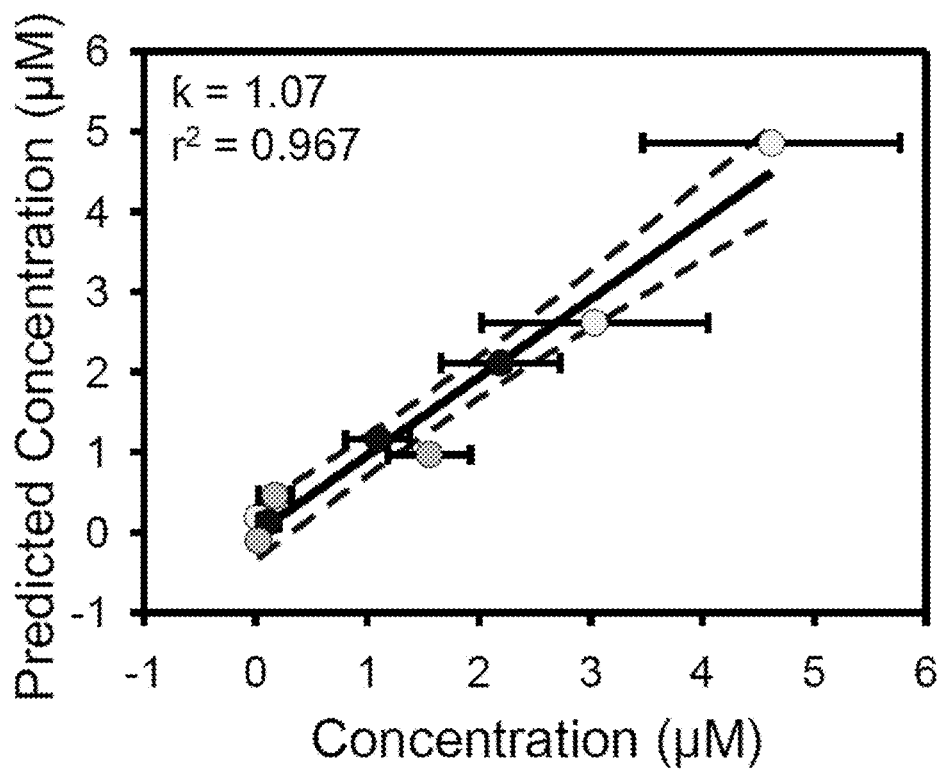
FIG. 16 is the correlation between the predicted and measured molecular concentrations of the molecule 1-3 under the given UEI ranging of 0-1.25.

FIG. 15 illustrates to give equal weight of each imaging index to UII, i.e., $w_1=0.25$, $w_2=0.25$, $w_3=0.25$, $w_4=0.25$, and $c_1=1$, $c_2=1$, $c_3=1$, $c_4=1$. FIG. 15 shows the measured concentrations of molecules 1-3 using the defined UII under the given UEI. The molecule 1 again has the highest penetration (the predicted concentration range is 1.7 µM to 6.2 µM during UEI ranging of 0.65-1.25), and the correlation between UII and molecule 1 penetration can be derived as: $C_{M1}=0.649 \cdot UII-0.608$, with the correlation of $r^2=0.975$, the $C_{M1}$ is the concentration of molecule 1. The molecule 2 has intermediate molecular penetration (the predicted concentration range is 0.7 µM to 3.1 µM during UEI ranging of 0.65-1.25), and the correlation between UII and the molecule 2 penetration can be derived as: $C_{M2}=0.276 \cdot UII-0.213$, with the correlation of $r^2=0.924$, the $C_{M2}$ is the concentration of molecule 2. The molecule 3 has the least molecular penetration (the predicted concentration range is 0.02 µM to 2.1 µM during UEI ranging of 0.65-1.25). The correlation between UII and the molecule 3 penetration can be derived as: $C_{M3}=0.149 \cdot UII-0.285$, with the correlation of $r^2=0.645$, the $C_{M3}$ is the concentration of molecule 3. That is able to further calibrate the relationship (using UII) between UEI with molecular penetration at least ranging of 1-150 kDa.

Integrating of the UEI and the UII by above uniform and calibrated method steps, in this embodiment, it is possible to examine the three molecular penetrations reflecting to the four imaging indexes with different UEIs. Another experiment is conducted, the three molecular penetrations was measured (shown in FIG. 10), and comparing to the quantified predict results of the UEI. The correlation of UEI is evaluated under the UII. The result is showed in FIG. 16.

In one embodiment, the correlation to integration procedure can be expressed a function G(.) with the input parameters which include UEI, UII, and molecular weight, MW, and maps to the eventual output, the molecular concentration, Cm, is defined as:

$$Cm = G(UEI, UII, MW).$$

The relationship can be rewritten to be a more detailed form to be:

$$Cm = G(f(P, \text{freq}, t_{on}), g(II1, \ldots, IIn), MW).$$

The n could be more than 1, it represents that a number of imaging indexes can be employed into this proposed technology.

In one embodiment, the Cm can be calculated as:

$$Cm = 3.6036 \cdot e^{(-0.01 \cdot MW)} \cdot UII + (-0.0013 \cdot MW + 0.2) = C_1 \cdot UII + C_2.$$

The coefficients $C_1 = 3.6036 \cdot e^{(-0.01 \cdot MW)}$ and $C_2 = 0.0013 \cdot MW + 0.2$.

In this embodiment, the correlation between predicted and measured molecular penetration is high ($r^2=0.967$), demonstrating the success of the proposed invention in using UII to predict the molecular concentration with a wide range of molecular size of 1-150 kDa.

To conclude, the whole concept of this invention comprises a two-hierarchical structure to perform for building a robust and precise method to estimate the molecular penetration in-vivo, due to relationship of the focused ultrasound exposure parameter and the molecular size during molecular delivery into CNS. The purpose of the first hierarchical process is to unify exposure input to the exposure conditions so as to build a transferred relation to imaging index. In short, the process includes: transformation from a plurality of exposure parameters to a defined UEI; then, employing the UEI to perform focused ultrasound exposure to the brain with the imaging contrast agent is administered; and observing the response to obtain readout from a plurality of imaging indexes. The purpose of the second hierarchical process is to unify imaging index to readout so as to build a reliable transferred relationship with molecular concentration. The process mainly includes: performing transformation from a plurality of imaging indexes readout to a defined UII, with the defined combination fashion; together with the given UEI, the responded UII, and known of the delivered molecular size, the transformation can be made to predict molecular penetration. In another words, linking these two processes, molecular penetration induced by ultrasound irradiation can be estimated from medical imaging under different ultrasound exposure conditions and various molecular sizes.

For example, in brain tumor treatment, metastasized to CNS, Herceptin (EGFR vIII antibody; 150 kDa) and D4-receptor antibodies (150 kDa) have potential to be applied. Avastin already demonstrated above is also a potential biologic drug for brain tumor therapy (150 kDa). A chemotherapeutic agents including doxorubicin (DOX; 543 Da), BCNU (250 Da), Temozolomide (194 Da), methotrexate (545 Da), all of them have been delivered into the normal rat brain. In Alzheimer's disease, therapeutic anti-amyloid-β antibodies (~150 kDa) have potentially to be enhanced delivered into CNS through the focused ultrasound technology. For Parkinson's disease, the neurotrophic factors such as GDNF and BDNF (14-32 kDa), or viral vectors carrying the neurotrophic factor genes (different serotypes ranging of several tens of kDa) all has potential to be employed in this technology. Besides, small interfering RNA (~13 kDa) can also be non-invasively delivered into the striatum to modulate the expression of mutant Huntingtin protein.

Using Herceptin (HER2-mAb) as an example (MW=150 kDa), employing FUS exposure with the pressure=0.8 MPa, center frequency=0.4 MHz, exposure time=120 s (these can transfer to UEI of 0.96), and obtained II1(fold)=5.868×UEI+1.314=6.94728, II2(fold)=3.253×UEI+0.908=4.03068, II3 (fold)=4.942×UEI+1.174=5.91832, and II4(fold)=8.972×UEI+1.486=10.09912, and convert to the UII=6.74885, then estimating the predicted Herceptin penetration could be 5.431860272 µM.

In another example, using BCNU, a chemotherapeutic agent for brain cancer therapy (MW=0.25 kDa), employing FUS exposure with the pressure=0.5 MPa, center frequency=0.8 MHz, exposure time=30 s (these can transfer to UEI of 0.15), and obtained II1(fold)=5.868×UEI+1.314=2.1942, II2(fold)=3.253×UEI+0.908=1.39575, II3 (fold)=4.942×UEI+1.174=1.9153, II4(fold)=8.972×UEI+1.486=2.8318, and convert to the UII=2.0842625, then estimating estimate the predicted BCNU penetration could be 7.692069676 µM.

In another example, using Adeno-associated viral vector (AAV), a commonly employed gene vector to perform CNS gene delivery (MW=50 kDa), employing FUS exposure with the pressure=1.2 MPa, center frequency=1 MHz, exposure time=60 s (these can transfer to UEI of 0.72), and obtained II1(fold)=5.868×UEI+1.314=5.53896, II2(fold)=3.253×UEI+0.908=3.24996, II3(fold)=4.942×UEI+1.174=4.73224, II4(fold)=8.972×UEI+1.486=7.94584, and convert to the UII=5.36675, then estimating the predicted BCNU penetration could be 11.86537266 µM.

The above embodiments show that the present invention has potential for CNS drug delivery, and the methods could be used to employ focused ultrasound locally, to enhance CNS blood-brain permeation, and to increase local therapeutic molecular penetration and deposition. Therapeutic molecules wouldn't penetrate or be limited by BBB, that all of them in this approach could be measured in-vivo by the delivery method of molecular penetration.

What is claimed is:
1. A method of an ultrasound-mediated delivery system to monitor molecular penetration comprising:
   providing a medical imaging system and an ultrasound system;

administering a microbubble agent to a capillary in a brain and concurrently applying a first ultrasonic wave to transiently permeate a blood-brain barrier (BBB);

determining a unified exposure index (UEI) with multiple exposure parameters of the ultrasound system;

applying a second ultrasound wave by the ultrasound system to open the blood-brain barrier (BBB) in the brain;

administering a contrast agent suitable for the medical imaging system to the brain;

analyzing multiple imaging data obtained from the medical imaging system to calculate at least one imaging index;

determining a unified imaging index (UII) by the at least one imaging index which comprises a first imaging index (II1), a second imaging index (II2), a third imaging index (II3) and a fourth imaging index (II4), wherein the first imaging index (II1) represents a molecule penetrating percentage of the contrast agent into the BBB, the second imaging index (II2) represents a total signal intensity change in a fixed time period, the third imaging index (II3) represents an influx permeability of the contrast agent, and the fourth imaging index (II4) represents a volume fraction change of the total molecular penetration into the brain; wherein the UII is described as: UII=g(II1,II2,II3,II4), wherein the g is a function defined as a linear weighted combination of the four imaging index (II1, II2, II3, and II4); and determining a concentration of the contrast agent delivered across the BBB using the UEI and the UII.

2. The method of claim 1, wherein the medical imaging system comprises a computed tomography equipment and a magnetic resonance imaging equipment.

3. The method of claim 1, wherein the ultrasound system is a focused ultrasound apparatus.

4. The method of claim 1, wherein the multiple exposure parameters comprise an exposure time, a center frequency, and a pressure.

5. The method of claim 1, wherein the contrast agent comprises a drug, and the drug is to treat neurological diseases and disorders.

6. The method of claim 5, wherein said drug comprises a molecular weight of 0.1 kDa to 200 kDa.

7. The method of claim 1, wherein the at least one imaging index comprises a first imaging index, a second imaging index, a third imaging index, and a fourth imaging index.

8. The method of claim 7, wherein the first imaging index represents a molecule penetrating percentage of the contrast agent in the blood-brain barrier.

9. The method of claim 7, wherein the second imaging index represents a total signal intensity change in a predetermined time period.

10. The method of claim 7, wherein the third imaging index represents an influx permeability of the contrast agent into the brain.

11. The method of claim 7, wherein the fourth imaging index represents a volume fraction change of total molecular penetration into the brain.

12. The method of claim 1, wherein the UII represents a second opening scale associated with an opening of the blood-brain barrier detected by the medical imaging system.

13. A method of an ultrasound-mediated delivery system to monitor molecular penetration comprising:

providing a dynamic contrast-enhanced magnetic resonance imaging system and a focused ultrasound apparatus;

administering a microbubble agent to a capillary in a brain and concurrently applying a first ultrasonic wave to transiently permeate a blood-brain barrier (BBB);

determining a unified exposure index (UEI) with multiple exposure parameters of the focused ultrasound apparatus;

applying a second ultrasound wave by the focused ultrasound to open the blood-brain barrier (BBB) in the brain;

administering a contrast agent suitable for the dynamic contrast-enhanced magnetic resonance imaging system to the brain;

analyzing multiple imaging data obtained from the dynamic contrast-enhanced magnetic resonance imaging system and based on pharmacokinetic and pharmacodynamic behavior to calculate at least one imaging index;

determining a unified imaging index (UII) by the at least one imaging index which comprises a first imaging index (II1), a second imaging index (II2), a third imaging index (II3) and a fourth imaging index (II4), wherein the first imaging index (II1) represents an immediate flush scale of the molecule penetrating into the BBB, the second imaging index (II2) represents an accumulated behavior of the penetrated molecules, the third imaging index (II3) represents a calculation of a blood-to-brain influx permeability and the fourth imaging index (II4) represents a calculation of a volume fraction change due to the BBB opening, wherein the UII is described as: UII=g(II1,II2,II3,II4), wherein the g is a function defined as a linear weighted combination of the four imaging index (II1, II2, II3, and II4); and determining a concentration of the contrast agent delivered across the BBB using the UEI and the UII.

14. The method of claim 13, wherein the first imaging index (II1) is described as:

$$II1 = \left(\frac{SI_{post} - SI_{pre}}{SI_{pre}} * 100\%\right)$$

wherein the $SI_{post}$ represents a signal intensity (SI) after the contrast agent administration, and the $SI_{pre}$ represents an SI before the contrast agent administration.

15. The method of claim 14, wherein the second imaging index (II2) is described as:

$$II2 = \left(\frac{\int_t C_{pt} \cdot dt}{V}\right)$$

wherein the $C_{pt}$ is vertical segments under a concentration curve area of the contrast agent, and the V is total volume of a region of interest (ROI).

16. The method of claim 15, wherein the third imaging index (II3) is described as $K_{trans}$, the fourth imaging index (II4) is described as $v_e$, and the II3 and II4 can be calculated from the following:

$$C_t(t) = v_p C_p(t) + K_{trans} \int_0^\tau C_p(t') \times e^{\left[\frac{-K_{trans}(t-t')}{v_e}\right]} dt'$$

$$= v_p C_p(t) + C_p(t) \otimes H(t)$$

wherein the $C_p(t)$ is the contrast agent concentration in a blood plasma, the $C_t(t)$ is the contrast agent concentration in the ROI, the $K_{trans}$ is a transfer rate constant from an intravascular system to an EES (per unit volume of tissue of the ROI), the $v_p$ is a capillary plasma volume of the contrast agent in the EES, the $v_e$ is a combination of the capillary plasma volume and a distribution volume of the contrast agent in the EES, and the H(t) is an impulse function and the $\otimes$ represents a convolution operation.

17. The method of claim 16, wherein the UEI is described as:

$$UEI=f(P,freq,t_{on})=P^a \times freq^b \times t_{on}$$

wherein the P represents a peak pressure (MPa), the freq is a center frequency (MHz) of the focused ultrasound apparatus exposure, and the $t_{on}$ is a total exposure time (sec.).

18. The method of claim 17, wherein the UII and the UEI are integrated to obtain the concentration of the contract agent (Cm), and the Cm is described as:

$$Cm=G(UEI,UII,MW)$$

wherein the G is a function and substitute parameters including the UEI, the UII, and molecular weight (MW) into the G.

19. The method of claim 13, wherein the contrast agent comprises a drug, and the drug is to treat neurological diseases and disorders.

20. The method of claim 1, wherein the UEI represents a first opening scale associated with an opening of the blood-brain barrier induced by the ultrasound system.

* * * * *